(12) United States Patent
Robinson

(10) Patent No.: US 6,214,872 B1
(45) Date of Patent: Apr. 10, 2001

(54) ARYLOXYARYLSULFONYLAMINO HYDROXAMIC ACID DERIVATIVES

(75) Inventor: Ralph Pelton Robinson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/380,163

(22) PCT Filed: Jul. 21, 1998

(86) PCT No.: PCT/IB98/01113

§ 371 Date: Aug. 26, 1999

§ 102(e) Date: Aug. 26, 1999

(87) PCT Pub. No.: WO99/07675

PCT Pub. Date: Feb. 18, 1999

Related U.S. Application Data

(60) Provisional application No. 60/055,207, filed on Aug. 8, 1997.

(51) Int. Cl.$^7$ .......................... C07C 311/29; A61K 31/19
(52) U.S. Cl. .......................... 514/530; 514/562; 514/329; 514/459; 546/223; 549/424; 560/13; 562/430
(58) Field of Search ................ 560/13; 562/430; 546/223; 549/424; 514/459, 329, 530, 562

(56) References Cited

U.S. PATENT DOCUMENTS 5,929,097 * 7/1999 Levin ................................... 514/351

FOREIGN PATENT DOCUMENTS

| 0606046 | * | 7/1994 | (EP) . |
| WO 96/275583 | * | 9/1996 | (WO) . |

* cited by examiner

Primary Examiner—Jane Fan
(74) Attorney, Agent, or Firm—Peter C. Richardson; Paul H. Ginsburg; Garth Butterfield

(57) ABSTRACT

A compound of the formula

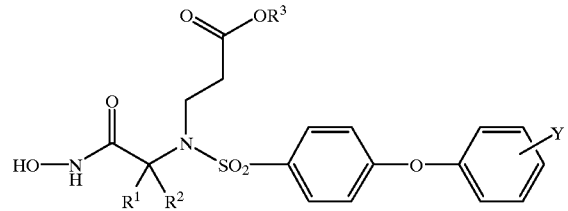

I wherein X, Y, R$^1$ and R$^2$ are as defined above, useful in the treatment of arthritis or cancer and other diseases involving selective inhibition of matrix metaloproteinase-13.

15 Claims, No Drawings

ARYLOXYARYLSULFONYLAMINO HYDROXAMIC ACID DERIVATIVES

This application is A 371 of PCT/IB98/01113 Jul. 21, 1998 now WO 99/07675 which claims benefit of 60/055,207 Aug. 8, 1997

BACKGROUND OF THE INVENTION

The present invention relates to aryloxyarylsulfonylamino hydroxamic acid derivatives. These compounds are selective inhibitors of matrix metalloproteinase-13 and as such are useful in the treatment of a condition selected from the group consisting of arthritis, cancer, tissue ulceration, restenosis, periodontal disease, epidermolysis bullosa, bone resorption, loosening of artificial joint implants, atherosclerosis, multiple sclerosis, occular angiogenisis (for example macular degeneration) and other diseases characterized by matrix metalloproteinase activity.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (J. Leuk. Biol., 52 (2): 244–248, 1992).

Tumor necrosis factor is recognized to be involved in many infectious and auto-immune diseases (W. Friers, FEBS Letters, 1991, 285, 199). Furthermore, it has been shown that TNF is the prime mediator of the inflammatory response seen in sepsis and septic shock (C. E. Spooner et al., Clinical Immunology and Immunopathology, 1992 62 11).

PCT Publication WO 96,27583, published Sep. 12, 1996 refers to certain arylsulfonylamino hydroxamic acids.

SUMMARY OF THE INVENTION

The present invention relates to a compound of the formula

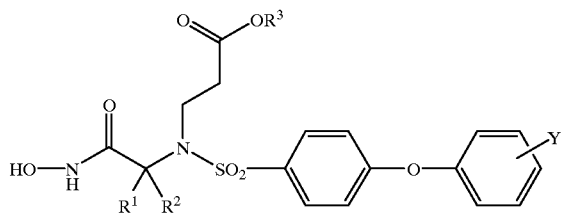

or the pharmaceutically acceptable salts thereof, wherein
$R^1$ is $(C_1-C_6)$alkyl;
$R^2$ is $(C_1-C_6)$alkyl;
or $R^1$ and $R^2$ taken together with the carbon atom to which they are attached form a ring selected from $(C_5-C_7)$ cycloalkyl, 4-tetrahydropyranyl and 4-piperidinyl;

$R^3$ is hydrogen or $(C_1-C_6)$alkyl; and
Y is a substituent on any of the carbon atoms of the phenyl ring capable of supporting an additional bond, preferably from 1 to 2 substituents (more preferably one substituent, most preferably one substituent in the 4-position) on the phenyl ring, independently selected from hydrogen, fluoro, chloro, trifluoromethyl, $(C_1-C_6)$ alkoxy, trifluoromethoxy, difluoromethoxy and $(C_1-C_6)$alkyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, enthanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compound of formula I may have chiral centers and therefore exist in different enantiomeric forms. This invention relates to all optical isomers and stereoisomers of the compounds of formula I and mixtures thereof.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include compounds of formula I in which the hydroxamic acid and carbonyl moiety when taken together form a group of the formula

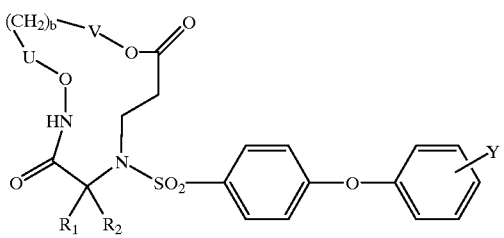

wherein $R^1$, $R^2$ and Y are as defined in formula I and U and V are independently carbonyl, methylene, $SO_2$ or $SO_3$, and b is an integer from one to three wherein each methylene group is optionally substituted with hydroxy.

Preferred compounds of formula I include those wherein Y is hydrogen, fluoro or chloro, preferably 4-fluoro or 4-chloro.

Other preferred compounds of formula I include those wherein $R^1$ and $R^2$ taken together with the carbon atom to which they are attached form a cyclopentyl or 4-tetrahydropyranyl ring.

Other preferred compounds of formula I include those wherein $R^1$ and $R^2$ are both methyl.

Other preferred compounds of formula I include those wherein $R^3$ is hydrogen.

Specific preferred compounds of formula I include the following:

3-[[4-(4-fluorophenoxy)benzenesulfonyl]-(1-hydroxy-carbamoylcyclopentyl)amino]-propionic acid ethyl ester,
3-[[4(4-fluorophenoxy)benzenesulfonyl]-(1-hydroxy-carbamoylcyclopentyl)amino]propionic acid,
3-[[4-(4-fluorophenoxy)benzenesulfonyl]-(1-hydroxycarbamoyl-1-methylethyl)amino]propionic acid ethyl ester, and
3-[[4-(4-fluorophenoxy)benzenesulfonyl]-(1-hydroxycarbamoyl-1-methylethyl)amino]propionic acid.

Other compounds of formula I include the following:

3-[[4-(4-fluorophenoxy)benzenesulfonyl]-(4-hydroxycarbamoyltetrahydropyran-4-yl)-amino]propionic acid,
3-[[4-(4-fluorophenoxy)benzenesulfonyl]-(4-hydroxycarbamoyltetrahydropyran-4-yl)-amino]propionic acid ethyl ester,
3-[[4-(4-chlorophenoxy)benzenesulfonyl]-(4-hydroxycarbamoyltetrahydropyran-4-yl)-amino]propionic acid,
3-[[4-(4-chlorophenoxy)benzenesulfonyl]-(4-hydroxycarbamoyltetrahydropyran-4-yl)-amino]propionic acid ethyl ester,
3-[(4hydroxycarbamoyltetrahydropyran-4-yl)-(4-phenoxybenzenesulfonyl)amino]-propionic acid.
3-[[(4-hydroxycarbamoyltetrahydropyran-4-yl)-(4-phenoxybenzenesulfonyl)amino]propionic acid ethyl ester,
3-[[4-(4-fluorophenoxy)benzenesulfonyl]-(4-hydroxycarbamoylpiperidin-4-yl)-amino]propionic acid ethyl ester,
3-[[4-(4-chlorophenoxy)benzenesulfonyl]-(1-hydroxycarbamoyl-1-methylethyl)amino]-propionic acid,
3-[[4-(4-chlorophenoxy)benzenesulfonyl]-(1-hydroxycarbamoyl-1-methylethyl)amino]propionic acid ethyl ester,
3-[[4-(4-fluorophenoxy)benzenesulfonyl]-(1-hydroxycarbamoylcyclohexyl)amino]-propionic acid,
3-[(1-hydroxycarbamoylcyclopentyl)-(4-phenoxybenzenesulfonyl)amino]propionic acid, and
3-[[4-(4-chlorophenoxy)benzenesulfonyl]-1-hydroxycarbamoylcyclopentyl)amino]-propionic acid.

The present invention also relates to a pharmaceutical composition for (a) the treatment of a condition selected from the group consisting of arthritis, cancer, tissue ulceration, restenosis, periodontal disease, epidermolysis bullosa, bone resorption, loosening of artificial joint implants, atherosclerosis, multiple sclerosis, occular angiogenisis (for example macular degeneration) and other diseases characterized by matrix metalloproteinase activity, or (b) the selective inhibition of matrix metalloproteinase-13 in a mammal, including a human, comprising an amount of a compound of claim 1 or a pharmaceutically acceptable salt thereof, effective in such treatments and a pharmaceutically acceptable carrier.

The present invention also relates to a method for the selective inhibition of matrix metalloproteinase-13 or in a mammal, including a human, comprising administering to said mammal an effective amount of a compound of claim 1 or a pharmaceutically acceptable salt thereof.

The present invention also relates to a method for treating a condition selected from the group consisting of arthritis, cancer, tissue ulceration, restenosis, periodontal disease, epidermolysis bullosa, bone resorption, loosening of artificial joint implants, atherosclerosis, multiple sclerosis, occular angiogenisis (for example macular degeneration) and other diseases characterized by matrix metalloproteinase-13 activity in a mammal, including a human, comprising administering to said mammal an amount of a compound of claim 1 or a pharmaceutically acceptable salt thereof, effective in treating such a condition.

DETAILED DESCRIPTION OF THE INVENTION

The following reaction Schemes illustrate the preparation of the compounds of the present invention. Unless otherwise indicated Y, $R^1$, $R^2$ and $R^3$ in the reaction Schemes and the discussion that follow are defined as above.

Scheme 1

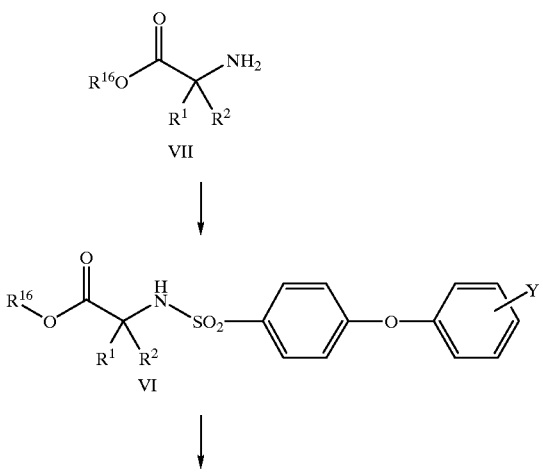

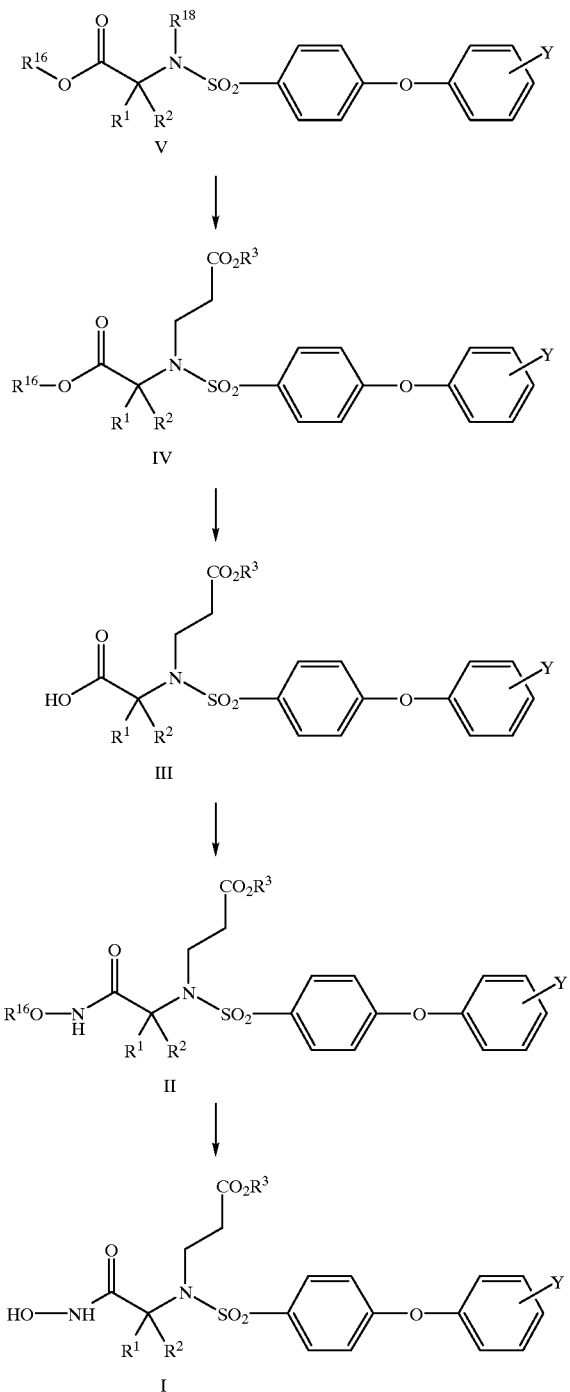

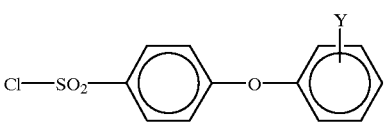

in the presence of a base, such as triethylamine, and a polar solvent, such as tetrahydrofuran, 1,2-dimethoxyethane, dioxane, water or acetonitrile, preferably 1,2-dimethoxyethane. The reaction mixture is stirred, at room temperature, for a time period between about 10 minutes to about 24 hours, preferably about 60 minutes.

The arylsulfonylamino compound of formula VI, wherein $R^{16}$ is benzyl, is converted to the corresponding compound of formula V, wherein $R^{18}$ is the group 3-tert-butyl-dimethylsilanyloxypropanyl by reaction with tert-butyl-(3-halo-propoxy)dimethylsilane, preferably the iodide derivative, in the presence of a base, such as potassium carbonate, cesium carbonate, potassium hexamethyldisilazide, or sodium hydride, preferably potassium hexamethyldisilazide. The reaction is stirred in a polar solvent, such as dimethylformamide or N-methylpyrrolidin-2-one, at room temperature, for a time period between about 2 hours to about 48 hours, preferably about 18 hours.

The compound of formula V is converted to a carboxylic acid derivative of formula IV by reaction with boron trifluoride-etherate complex to form an intermediate alcohol, followed by oxidation and protection by esterification. Specifically, the reaction with boron trifluoride-etherate complex is performed in an inert solvent such as methylene chloride, chloroform, preferably methylene chloride, at room temperature for about 15 minutes to about 4 hours, preferably about one hour. Oxidation of the alcohol is facilitated by using chromium trioxide in aqueous sulfuric acid (Jones Reagent) at about 0° C. for about one to about 6 hours, preferably about 2 hours. Protection of the carboxylic acid is facilitated by treatment of the free acid with an alkylating agent such as $R^3$—L, wherein L is a leaving group such as iodo, bromo, mesylate, or tosylate, preferably iodo, with a base, such potassium carbonate or cesium carbonate, preferably potassium carbonate, in a polar solvent such as dimethylformamide, N-methylpyrrolidin 2-one or tetrahydrofuran, preferably dimethyl formamide, for about 1 to about 24 hours, preferably 16 hours, at about room temperature.

The compound of formula IV is converted to a compound of formula III by removal of the $R^{16}$ protecting group by hydrogenolysis using palladium on carbon in a solvent such as methanol or ethanol, for a period from about 30 minutes to about 48 hours, preferably 16 hours, at a temperature of about 20° C. to about 25° C., i.e. room temperature.

The carboxylic acid compound of formula III is converted to the hydroxamic acid derivative of formula II, wherein $R^{16}$ is benzyl, by activation of the compound of formula III followed by reaction with benzylhydroxylamine. The compound of formula III is activated by treatment with (benzotriazol-1-yloxy)tris(dimethylamino) phosphonium hexafluorophosphate in the presence of a base, at room temperature, in a polar solvent. The aforesaid reaction is conducted for a period of about 15 minutes to about 4 hours, preferably about 1 hour. The activated compound derived from formula III is converted in situ to the compound of formula II by reaction with benzylhydroxylamine hydrochloride. The reaction with benzylhydroxylamine hydro- Scheme 1 refers to the preparation of compounds of the formula I from compounds of the formula VII. Referring to Scheme 1. the amino acid compound of formula VII, wherein $R^{16}$ is benzyl, is converted to the corresponding compound of formula VI by reaction with a reactive functional derivative of an arylsulfonic acid compound of the formula chloride is conducted for about 1 hour to about 5 days, preferably for about 16 hours, at a temperature of about 40° C. to about 80° C., preferably about 60° C. Suitable bases include N-methylmorpholine or diisopropylethylamine, preferably diisopropylethylamine. Suitable solvents include N,N-dimethylformamide or N-methylpyrrolidin-2one, preferably N,N-dimethylformamide.

The compound of formula II is converted into a compound I by removal of the hydroxyl amine protecting group. Removal of the hydroxylamine protecting group is carried out by hydrogenolysis of the benzyl protecting group using catalytic palladium on barium sulfate in a polar solvent at a temperature from about 20° C. to about 25° C., i.e. room temperature, for a period of about 1 hour to about 5 hours, preferably about 3 hours.

Compounds of formula VII and VIII are commercially available or can be made by methods well known to those of ordinary skill in the art.

Pharmaceutically acceptable salts of the acidic compounds of the invention are salts formed with bases, namely cationic salts such as alkali and alkaline earth metal salts, such as sodium, lithium, potassium, calcium, magnesium, as well as ammionium salts, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ is hydrogen, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the MMP-13 selective compounds of the present invention) to inhibit matrix metalloproteinase-13 (collagenase 3) and, consequently, demonstrate their effectiveness for treating diseases characterized by matrix metalloproteinase-13 is shown by the following in vitro assay tests.

Biological Assay

Inhibition of Human Collagenase (MMP-1)

Human recombinant collagenase is activated with trypsin using the following ratio: 10 mg trypsin per 100 mg of collagenase. The trypsin and collagenase are incubated at room temperature for 10 minutes then a five fold excess (50 mg/10 mg trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 ml is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 mM in assay buffer. The assay is initiated by the addition of 50 ml substrate per well of the microfluor plate to give a final concentration of 10 mM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). IC$_{50}$'s are determined from the concentration of inhibitor that gives a signal that is 50% of the control.

If $IC_{50}$'s are reported to be <0.03 mM then the inhibitors are assayed at concentrations of 0.3 mM, 0.03 mM, 0.03 mM and 0.003 mM.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 mM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 mM, 3 mM, 0.3 mM, and 0.03 mM.

Substrate (Dnp-Pro-Cha-Gly-Cys(Me)-His-Ala-Lys (NMA-NH2) is prepared as for inhibition of human collagenase (MMP-1) and 50 ml is added to each well to give a final assay concentration of 10 mM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 mM, inhibitors are then assayed at final concentrations of 0.3 mM, 0.03 mM, 0.003 mM and 0.0003 mM.

The compounds of the present invention possess surprisingly selective activity against matrix metalloproteinase-13 (collagenase 3) as compared to matrix metalloproteinase-1 (collagenase 1). Specifically, the compounds of the formula I are 100 times more selective for matrix metalloproteinase-13 (collagenase 3) than matrix metalloproteinase-1 (collagenase 1) and have $IC_{50}$'s of less than 10 nM against matrix metalloproteinase-13 (collagenase 3). Table 1 lists several compounds that demonstrate the unexpected selectivity of the compounds of the invention.

TABLE 1

I

| Ex. | $R^1$ | $R^2$ | $R^3$ | R | MMP-1 $IC_{50}$(nM) | MMP-13 $IC_{50}$(nM) |
|---|---|---|---|---|---|---|
| 1 | cyclopentyl | — | ethyl | 4-fluorophenoxy | 100 | 0.9 |
| 1 | cyclopentyl | — | ethyl | 4-fluorophenoxy | 100 | 0.9 |
| 2 | cyclopentyl | — | hydrogen | 4-fluorophenoxy | 360 | 1.2 |
| 2 | cyclopentyl | — | hydrogen | 4-fluorophenoxy | 200 | 0.6 |
| 3 | methyl | methyl | ethyl | 4-fluorophenoxy | 1200 | 1.6 |
| 3 | methyl | methyl | ethyl | 4-fluorophenoxy | 1800 | 2.3 |
| 4 | methyl | methyl | hydrogen | 4-fluorophenoxy | 3500 | 5.7 |
| 4 | methyl | methyl | hydrogen | 4-fluorophenoxy | 2000 | 2.3 |
| 4 | methyl | methyl | hydrogen | 4-fluorophenoxy | 4800 | 8 |
|  | cyclopentyl | — | hydrogen | methoxy | 800 | 21 |
|  | cyclopentyl | — | hydrogen | methoxy | 700 | 25 |
|  | methyl | methyl | hydrogen | methoxy | 12000 | 590 |
|  | methyl | methyl | hydrogen | methoxy | 12000 | 730 |
|  | cyclohexyl | hydrogen | hydrogen | methoxy | 18 | 4 |
|  | cyclohexyl | hydrogen | hydrogen | methoxy | 22 | 2 |

For administration to humans for the inhibition of matrix metalloproteinase-13 or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/g. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The following Examples illustrate the preparation of the compounds of the present invention. Melting points are uncorrected. NMR data are reported in parts per million (δ) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20 to 25° C. All non-aqueous reactions were run under a nitrogen atmosphere for convenience and to maximize yields. Concentration at reduced pressure means that a rotary evaporator was used.

EXAMPLE 1

3-[[4-(4-FLUOROPHENOXY) BENZENESULFONYL]-(1-HYDROXY-CARBAMOYL CYCLOPENTYL)AMINO]-PROPIONIC ACID ETHYL ESTER (A) To a solution of 1-aminocyclopentanecarboxylic acid benzyl ester p-toluenesulfonic acid salt (200 grams, 0.51 mole) and triethylamine (177 mL, 1.27 mole) in water (1 L) and 1,2-dimethoxyethane (1 L) was added 4-(4-fluorophenoxy)benzenesulfonyl-chloride (161 grams, 0.56 moles). The mixture was stirred at room temperature for 16 hours and then most of the solvent was removed by evaporation under vacuum. The mixture was diluted with ethyl acetate and was washed successively with dilute hydrochloric acid solution, water, and brine. The solution was dried over magnesium sulfate and concentrated to leave a brown solid. Trituration with diethyl ether to afforded 1-[4-(4-fluorophenoxy)benzenesulfonylamino]-cyclopentanecarboxylic acid benzyl ester as a tan solid, 167 grams (70%).

(B) To a solution of 1-[4-(4-fluorophenoxy)benzenesulfonylamino]-cyclopentanecarboxylic acid benzyl ester (199 grams, 0.42 mole) in dry N,N-dimethylformamide (2.5 L) at room temperature was added potassium hexamethyldisilazide (100 grams, 0.50 mole) and, after 3 hours, tert-butyl-(3-iodopropoxy)dimethylsilane (150 grams, 0.50 mole). The resulting mixture was stirred at room temperature for 16 hours. Additional tert-butyl-3-iodopropoxy)-dimethylsilane (20 grams, 0.067 mole) was then added. Stirring at room temperature was continued for a further 3.5 hours. The mixture was quenched by addition of saturated ammonium chloride solution. The N,N-dimethylformamide was removed by evaporation under vacuum. The residue was taken up in diethyl ether and washed with water and brine. After drying over magnesium sulfate, the diethyl ether was evaporated to afford crude 1-{[3-(tert-butyl-dimethylsilanyloxy)-propyl]-[4-(4-fluorophenoxy) benzenesulfonyl]-amino}cyclopentanecarboxylic acid benzyl ester as an amber oil (279.6 grams).

(C) To a solution of the crude 1{[3-(tert-butyl-dimethylsilanyloxy)-propyl]-[4-(4-fluorophenoxy) benzenesulfonyl]-amino}cyclopentanecarboxylic acid benzyl ester (279 grams) in methylene chloride (1 L) at room temperature was added boron trifluoride etherate (103 mL, 0.84 mole). After 1 hour, the reaction was quenched by sequential addition of saturated ammonium chloride solution and water. The organic phase was separated, washed with water and brine and dried over magnesium sulfate. Evaporation of the solvent under vacuum provided crude 1-[[4-(4-fluorophenoxy)benzenesulfonyl]-(3-hydroxypropyl)amino]cyclopentanecarboxylic acid benzyl ester as an amber oil (235 grams).

(D) A solution of the crude 1-[[4-(4-fluorophenoxy) benzenesulfonyl]-(3-hydroxypropyl)amino] cyclopentanecarboxylic acid benzyl ester (235 grams) in acetone (2 L) was cooled in an ice bath and treated with Jones reagent (about 200 mL) until an orange color persisted. The mixture was stirred from 0° C. to room temperature over 1 hour. After quenching excess oxidant with isopropanol (10 mL), the mixture was filtered and the filtrate was concentrated under vacuum. The residue was taken up in ethyl acetate, washed with water and brine, dried over magnesium sulfate and concentrated to afford a solid which was triturated with a mixture of diethyl ether and hexane to provide 1{(2-carboxyethyl)-[4-(4-fluorophenoxy) benzenesulfonyl]amino}cyclopentane carboxylic acid benzyl ester as a white solid (147 grams).

(E) To a solution of 1{(2-carboxyethyl)-[4-(4-fluorophenoxy)benzenesulfonyl] amino}cyclopentanecarboxylic acid benzyl ester (147 grams) in N,N-dimethyl formamide (3 L) at room temperature was added potassium carbonate (150 grams, 1.08 mole) and ethyl iodide (32.4 mL, 0.405 mole). The mixture was stirred for 16 hours at room temperature. After filtration, most of the solvent was removed under vacuum. The residue was taken up in water and acidified using 6N aqueous hydrogen chloride solution. The resulting mixture was extracted with diethyl ether. The organic extract was washed with water and brine, dried over magnesium sulfate, and concentrated to yield 1{(2-ethoxycarbonylethyl)-[4-(4-fluorophenoxy)benzenesulfonyl]amino}cyclopentane carboxylic acid benzyl ester as a yellow semi-solid (149.1 grams, 96%).

(F) A solution of 1{(2-ethoxycarbonylethyl)-4-(4-fluorophenoxy)benzene sulfonyl] amino}cyclopentanecarboxylic acid benzyl ester (74.5 grams, 0.13 mole) in ethanol (1.8 L) was treated with 10% palladium on activated carbon (7.4 grams) and hydrogenated in a Parr™ shaker at 3 atmospheres pressure for 16 hours. After filtration through nylon (pore size 0.45 μm) to remove the catalyst, the solvent was evaporated to afford 1{(2-ethoxycarbonylethyl)-[4-(4-fluorophenoxy) benzenesulfonyl]amino}cyclopentanecarboxylic acid as a white foam. The reaction was repeated on tie same scale to provide, in total, 125.2 grams of the desired product.

(G) Diisopropylethylamine (50 mL, 0.286 mole) and (benzotriazol-1-yloxy)tris-(dimethylamino)phosphonium hexafluorophosphate (126.5 grams, 0.286 mole) were added sequentially to a solution of 1{(2ethoxycarbonylethyl)-[4-(4-(4fluorophenoxy)benzenesulfonyl] amino}cyclopentanecarboxylic acid (125.2 grams, 0.26 mole) in N,N-dimethylformamide (2 L). The mixture was stirred for 1 hour. Additional diisopropylethylamine (91 mL, 0.52 mole) and O-benzylhydroxylamine hydrochloride (53.8 grams, 0.338 mole) were then added and the resulting mixture was stirred at 60° C. for 96 hours. After concentration under vacuum, the residue was taken up in water and acidified with 1N aqueous hydrogen chloride solution. The mixture was extracted with ethyl acetate and the extract was washed sequentially with water, saturated aqueous sodium bicarbonate solution and brine. The solution was dried over magnesium sulfate and concentrated to give crude 3{(1-benzyloxycarbamoylcyclopentyl)-[4-(4-fluorophenoxy) benzenesulfonyl]amino}propionic acid ethyl ester as a yellow oil (164 grams).

F) A solution of crude 3{(1-benzyloxycarbamoylcyclopentyl)-[4-(4-fluorophenoxy) benzenesulfonyl]amino}propionic acid ethyl ester (164 grams) in ethanol (2.4 L) was treated with 5% palladium on barium sulfate (50 grams) and hydrogenated in a Parr™ shaker at 3 atmospheres pressure for 3 hours. After filtration through nylon (pore size 0.45 μm) to remove the catalyst, the solvent was evaporated to afford an oil. After addition of ethyl acetate and hexane, 3-[[4-(4-fluorophenoxy) benzenesulfonyl]-(1-hydroxy-carbamoylcyclopentyl) amino]-propionic acid ethyl ester, a white crystalline solid (73.5 grams) was collected by filtration. The filtrate was concentrated and the residue was chromatographed on silica gel eluting with 40% ethyl acetate hexane to provide more of the desired product (32.5 grams).

Mp: 79–83° C. $^1$H NMR (DMSO-d$_6$): δ10.40 (br s, 1 H), 8.78 (br s, 1 H), 7.80–7.77 (m, 2 H), 7.31–7.03 (m, 6 H), 4.02 (q, J=7.3 Hz, 2 H), 3.49–3.45 (m, 2 H), 2.70–2.67 (m, 2 H), 2.24–2.21 (m, 2 H), 1.86–1.83 (m, 2 H), 1.53–1.50 (m, 4 H), 1.16 (t, J=7.3 Hz, 3 H). MS 493 (M−1). Analysis calculated for $C_{23}H_{27}FN_2O_7S \cdot H_2O$: C, 53.90; H, 5.70; N, 5.47. Found : C, 54.52; H, 5.63; N, 5.27.

EXAMPLE 2

3-[[4-(4-FLUOROPHENOXY) BENZENESULFONYL]-(1-HYDROXY-CARBAMOYLCYCLOPENTYL)AMINO] PROPIONIC ACID

A solution of 3-[[4-(4fluorophenoxy)benzenesulfonyl]-1-hydroxycarbamoyl cyclopentyl)-amino]propionic acid ethyl ester (106 grams, 0.214 mole) in ethanol (2.5 L) was treated with aqueous 1 N sodium hydroxide solution (856 mL, 0.856 mole) and stirred at room temperature for 2 hours. The mixture was concentrated to remove ethanol, diluted with water, acidified with 6 N aqueous hydrochloric acid solution and extracted with ethyl acetate. After washing with water and brine, the organic extract was dried over magnesium sulfate and concentrated to a foam. Crystallization from 30% ethyl acetate in hexane gave 3-[[4-(4-fluorophenoxy) benzenesulfonyl]-(1-hydroxy carbamoylcyclopentyl)-amino]propionic acid as a white crystalline solid (81.5 grams, 81%).

Mp: 170–172° C. $^1$ H NMR (DMSO-d$_6$): δ12.25 (br s, 1 H), 10.40 (br s, 1 H), 8.74 (br s, 1 H), 7.79–7.77 (m, 2 H), 7.29–7.03 (m, 6 H), 3.45–3.41 (m, 2 H), 2.61–2.57 (m, 2 H), 2.24–2.21 (m, 2 H), 1.88–1.82 (m, 2 H), 1.53–1.50 (m, 4 H). MS 465 (M−1). Analysis calculated for $C_{21}H_{23}FN_2O_7S$: C, 54.07; H, 4.97; N, 6.00. Found: C, 54.17; H, 5.02; N, 6.05.

EXAMPLE 3

3-[[4-(4-FLUOROPHENOXY) BENZENESULFONYL]-(1-HYDROXYCARBAMOYL-1-METHYLETHYL) AMINO]PROPIONIC ACID ETHYL ESTER

The title compound was prepared according to a procedure analogous to that outlined in Example 1 starting with 2-amino2-methyl-propionic acid benzyl ester p-toluenesulfonic acid salt.

Mp: 124.8–125° C. $^1$H NMR (DMSO-d$_6$) δ10.37 (s, 1 H), 8.74 (s,1 H), 7.86 (d, 2 H, J=8.9 Hz), 7.16–7.30 (m, 4 H), 7.04 (d, 2 H, J=8.7 hz), 3.99 (q, 2 H, J=7.1 Hz), 3.33–3.37 (m, 2 H), 2.62–2.66 (m, 2 H), 1.40 (s, 6 H), 1.13 (t, 3 H, J=7.1 Hz). MS: 467 (M−1). Analysis calculated for $C_{21}H_{25}FN_2O_7S$: C, 53.84; H, 5.38; N, 5.98. Found: C, 54.00; H, 5.12; N, 5.87.

EXAMPLE 4

3-[[4-(4-FLUOROPHENOXY) BENZENESULFONYL]-(1-HYDROXYCARBAMOYL-1-METHYLETHYL) AMINO]PROPIONIC ACID

The title compound was prepared from 3-[[4-(4-fluorophenoxy)benzenesulfonyl]-(1-hydroxycarbamoyl-1-methylethyl)amino]propionic acid ethyl ester according to a procedure analogous to that described in Example 2.

Mp: 162–162.5° C. MS: 439 (M−1). $^1$H NMR (DMSO-d$_6$) δ12.26 (s, 1 H) 10.10.38 (s, 1 H), 8.75 (s, 1 H), 7.86–7.88 (m, 2 H), 7.16–7.7.30 (m, 4 H), 7.03–7.06 (m, 2 H), 3.29–3.35 (m, 2 H), 2.47–2.59 (m, 2 H), 1.40 (s, 6 H).

What is claimed is:

1. A compound of the formula

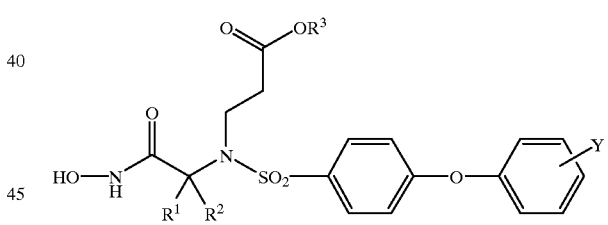

I or the pharmaceutically acceptable salts thereof, wherein $R^1$ is $(C_1-C_6)$alkyl;

$R^2$ is $(C_1-C_6)$alkyl;

or $R^1$ and $R^2$ taken together with the carbon atom to which they are attached form a ring selected from $(C_5-C_7)$ cycloalkyl, 4-tetrahydropyranyl and 4-piperidinyl;

$R^3$ is hydrogen or $(C_1-C_6)$alkyl; and

Y is a substituent on any of the carbon atoms of the phenyl ring capable of supporting an additional bond, independently selected from fluoro, chloro, trifluoromethyl, $(C_1-C_6)$alkoxy, trifluoromethoxy, difluoromethoxy and $(C_1-C_6)$alkyl.

2. A compound according to claim 1, wherein Y is hydrogen, fluoro or chloro.

3. A compound according to claim 1, wherein Y is 4-fluoro or 4-chloro.

4. A compound according to claim 1, wherein $R^1$ and $R^2$ taken together with the carbon atom to which they are attached form a cyclopentyl ring.

5. A compound according to claim 3, wherein $R^1$ and $R^2$ taken together with the carbon atom to which they are attached form a cyclopentyl ring.

6. A compound according to claim 1, wherein $R^1$ and $R^2$ taken together with the carbon atom to which they are attached form a 4-tetrahydropyranyl ring.

7. A compound according to claim 1, wherein $R^1$ and $R^2$ are both methyl.

8. A compound according to claim 3, wherein $R^1$ and $R^2$ are both methyl.

9. A compound according to claim 1, wherein $R^3$ is hydrogen.

10. A compound according to claim 3, wherein $R^3$ is hydrogen.

11. A compound according to claim 4, wherein $R^3$ is hydrogen.

12. A compound according to claim 1, wherein said compound is selected from the group consisting of:

3-[[4-(4-fluorophenoxy)benzenesulfonyl]-(1-hydroxycarbamoylcyclopentyl)amino]-propionic acid ethyl ester,
3-[[4-(4-fluorophenoxy)benzenesulfonyl]-(1-hydroxycarbamoylcyclopentyl)amino]propionic acid,
3-[[4-(4-fluorophenoxy)benzenesulfonyl]-(1-hydroxycarbamoyl-1-methylethyl)amino]propionic acid ethyl ester, and
3-[[4-(4-fluorophenoxy)benzenesulfonyl]-(1-hydroxycarbamoyl-1-methylethyl)amino]propionic acid.

13. A pharmaceutical composition for (a) the treatment of arthritis or cancer and other diseases characterized by matrix metalloproteinase-13 activity or (b) the selective inhibition of matrix metalloproteinase-13 in a mammal, including a human, comprising an amount of a compound of claim 1 or a pharmaceutically acceptable salt thereof, effective in such treatments or inhibition and a pharmaceutically acceptable carrier.

14. A method for the selective inhibition of matrix metalloproteinases-13 in a mammal, including a human, comprising administering to said mammal an effective amount of a compound of claim 1 or a pharmaceutically acceptable salt thereof.

15. A method for treating arthritis or cancer and other diseases characterized by matrix metallproteinase-13 activity in a mammal, including a human, comprising administering to said mammal an amount of a compound of claim 1 or a pharmaceutically acceptable salt thereof, effective in treating such a condition.

* * * * *